(12) United States Patent
Park et al.

(10) Patent No.: US 11,760,792 B2
(45) Date of Patent: Sep. 19, 2023

(54) GRP78-DERIVED PEPTIDE FOR IDENTIFYING HIGH-EFFICIENCY STEM CELLS

(71) Applicants: NIBEC CO., LTD., Chungcheongbuk-do (KR); CHUNGBUK NATIONAL UNIVERSITY INDUSTRY ACADEMIC COOPERATION FOUNDATION, Chungcheongbuk-do (KR); SEOUL NATIONAL UNIVERSITY R&DB FOUNDATION, Seoul (KR)

(72) Inventors: Yoon Shin Park, Chungcheongbuk-do (KR); Yoon Jeong Park, Seoul (KR); Chong-Pyoung Chung, Seoul (KR); Jue-Yeon Lee, Gyeonggi-do (KR)

(73) Assignees: NIBEC CO., LTD., Chungcheongbuk-do (KR); CHUNGBUK NATIONAL UNIVERSITY INDUSTRY ACADEMIC COOPERATION FOUNDATION, Seoul (KR); SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 87 days.

(21) Appl. No.: 16/755,373

(22) PCT Filed: Oct. 15, 2018

(86) PCT No.: PCT/KR2018/012118
§ 371 (c)(1),
(2) Date: Apr. 10, 2020

(87) PCT Pub. No.: WO2019/074343
PCT Pub. Date: Apr. 18, 2019

(65) Prior Publication Data
US 2020/0369753 A1    Nov. 26, 2020

(30) Foreign Application Priority Data
Oct. 13, 2017   (KR) .................. 10-2017-0133614

(51) Int. Cl.
| | |
|---|---|
| *A61K 38/10* | (2006.01) |
| *G01N 33/53* | (2006.01) |
| *G01N 33/58* | (2006.01) |
| *G01N 33/68* | (2006.01) |
| *C07K 7/08* | (2006.01) |
| *C07K 9/00* | (2006.01) |
| *C07K 16/18* | (2006.01) |
| *G01N 33/50* | (2006.01) |

(52) U.S. Cl.
CPC .............. *C07K 16/18* (2013.01); *A61K 38/10* (2013.01); *C07K 7/08* (2013.01); *C07K 9/00* (2013.01); *G01N 33/5073* (2013.01); *G01N 33/53* (2013.01); *G01N 33/582* (2013.01); *G01N 33/68* (2013.01); *C07K 2319/00* (2013.01); *C07K 2319/40* (2013.01); *C07K 2319/60* (2013.01)

(58) Field of Classification Search
CPC .... A61K 38/1709; A61K 38/04; A61K 38/10; A61K 38/17; C07K 14/47; C07K 7/08; C07K 2319/00; C07K 2319/40; C07K 2319/60; G01N 33/582
See application file for complete search history.

(56) References Cited

U.S. PATENT DOCUMENTS

| 8,227,413 B2 * | 7/2012 | Hardy ....................... A61P 9/04 |
| | | 514/13.3 |
| 2001/0034042 A1 * | 10/2001 | Srivastava .............. A61P 31/00 |
| | | 435/68.1 |
| 2010/0135904 A1 | 6/2010 | Gray et al. |

FOREIGN PATENT DOCUMENTS

| CN | 101445551 A | 6/2009 |
| KR | 20090045940 A | 5/2009 |
| KR | 1020100012153 A | 8/2012 |
| KR | 10-2014-0146859 A | 4/2015 |
| KR | 20160043927 A | 4/2016 |
| WO | 2011119484 A1 | 9/2011 |
| WO | 2013040142 A2 | 3/2013 |

(Continued)

OTHER PUBLICATIONS

Bhattacharya et al. Impact of genetic variation on three dimensional structure and function of proteins. PLoS ONE 12(3): e0171355, 2017.*

(Continued)

*Primary Examiner* — Bridget E Bunner
(74) *Attorney, Agent, or Firm* — Elmore Patent Law Group, P.C.; Joseph C. Zucchero; Carolyn S. Elmore

(57) ABSTRACT

The present invention relates to a GRP78-derived peptide for screening highly efficient stem cells and the use thereof, and more particularly, to screening highly efficient stem cells using, as a marker, a GRP78-derived peptide capable of binding to the binding domain of GRP78 protein on the cell surface. According to the present invention, the GRP78-derived peptide comprising only a specific amino acid sequence capable of recognizing highly efficient stem cells, among the amino acid sequence of GRP78, makes it possible to screen only non-senescent young stem cells. In addition, when stem cells are treated with the GRP78-derived peptide or the GRP78-derived peptide is introduced into stem cells, the efficiency of the stem cells can be increased. Thus, the GRP78-derived peptide is useful for the production of stem cell therapy products having excellent efficacy.

7 Claims, 6 Drawing Sheets

Specification includes a Sequence Listing.

(56) References Cited

FOREIGN PATENT DOCUMENTS

| WO | 2014107718 A2 | 7/2014 |
| WO | 2014160465 A2 | 10/2014 |
| WO | 2017176067 A1 | 12/2017 |

OTHER PUBLICATIONS

Bork, P. Powers and pitfalls in sequence analysis: the 70% hurdle. Genome Res 10: 398-400, 2000.*
Bork, P. Go hunting in sequence databases but watch out for the traps. Trends in Genetics 12(10): 425-427, 1996.*
Brenner. S.E. Errors in genome annotation. Trends in Genetics 15:132-133, 1999.*
Casas, C. GRP78 at the centre of the stage in cancer and neuroprotection. Front Neurosci 11: 177, 2017.*
Chao et al. A direct-repeat sequence of the human BiP gene is required for A23187-medited inducibility and an inducible nuclear factor binding. Nucleic Acids Res 20(24): 6481-6485, 1992.*
Chiu et al. Grp78 as a therapeutic target for refractory head-neck cancer with CD24-CD44+ stemness phenotype. Cancer Gene Therapy 20: 606-615, 2013.*
Conner et al. Cell surface GRP78 promotes sternness in normal and neoplastic cells. Sci Reports 10: 3474, 2020.*
Doerks et al. Protein annotation: detective work for function prediction. Trends in Genetics 14:248-250, 1998.*
Fenton et al. Rheostat positions: a new classification of protein positions relevant to pharmacogenomics. Medicinal Chem Res 29: 1133-1146, 2020.*
Guo et al. Protein tolerance to random amino acid change. Proc Natl Acad Sci USA 101(25): 9205-9210, 2004.*
Hu et al. Targeting oral cancer sternness and chemoresistance by isoliquiritigenin-mediated GRP78 regulation. Oncotarget 8(55): 93912-93923, 2017.*
Lee et al. Hypoxic preconditioning promotes the bioactivities of mesenchymal stem cells via the HIF-1alpha-GRP78-Akt axis. Int J Mol Studies 18: 1320, 2017.*
Nami et al. Overexpression of molecular chaperons GRP78 and GRP94 in CD44hi/CD24lo breast cancer stem cells. Bioimpacts 6(2): 105-110, 2016.*
Ngo et al. "Computational complexity, protein structure prediction, and the Levinthal paradox" in The Protein Folding Problem and Tertiary Structure Prediction, pp. 492-495, 1994.*
Peng et al. GRP78 secreted by tumor cells stimulates differentiation of bone marrow mesenchymal stem cells to cancer-associated fibroblasts. Biochem Biophys Res Comm 440: 558-563, 2013.*
Skolnick et al. From genes to protein structure and function: novel applications of computational approaches in the genomic era. Trends Biotechnol 18(I):34-39 2000.*
Smith et al. The challenges of genome sequence annotation or "the devil is in the details". Nature Biotechnol 15: 1222-1223, 1997.*
Ting et al. Human gene encoding the 78,000-dalton glucose-regulated protein and its pseudogene: structure, conservation, and regulation. DNA 7: 275-286, 1988.*
Tokuriki et al. Stability effects of mutations and protein evolvability. Curr Opin Structural Biol 19: 596-604, 2009.*
Wells, J.A. Additivity of mutational effects in proteins. Biochemistry 29(37): 8509-8517, 1990.*
Wisniewska et al. Crystal structures of the ATPase domains of four human Hsp70 isoforms: HSPA1L/Hsp70-hom, HSPA2/Hsp70-2, HSPA6/Hsp70B, and HSPA5/BiP/GRP78. PLoS One 5(1): e8625, 2010.*
Wang et al. HSPA5 gene encoding Hsp70 chaperone BiP in the endoplasmic reticulum. Gene 618: 14-23, online Mar. 2017.*
Hardy, B. et al., "PD 09/19 Isolation, Characterization and Clinical Relevance of Tumor Stem Cells Expressing Membrane GRP78 in Colon Cancer", European J. of Immun., 39(S1), https://onlinelibrary.wiley.com/doi/epdf/10.1002/eji.200990184, Aug. 19, 2009, S511.
Supplementary Partial European Search Report dated May 14, 2021 for EP Patent Application No. 18 866 139.1.
Kenichi, Miharada et al., Cell Stem Cell (2011), vol. 9, pp. 330-344.
Li, W. et al., "Proteomics Analysis of Normal and Senescent NG108-15 Cells: GRP78 Plays a Negative Role in Cisplatin-induced Senescence in the NG108-15 Cell Line", Plos One, Mar. 2014, vol. 9, No. 3, e90114, pp. 1-11.
Li, W. et al., "Cisplatin-induced Senescene in Ovarian Cancer Cells is Mediated by GRP 78", Oncology Reports, 2014, vol. 31, pp. 2525-2534.
Svendsen, C. "Adult versus embryonic stem cells: which is the way forward?" Trends in Neurosciences 23:450, 2000.
Song et al. "Aged Human multipotent mesenchymal stromal cells can be rejuvenated by neuron-derived neurotrophic factor and improve heart function after injury", JACC: Basic to Translational Science 2:702-716, 2017.
Peffers et al. "Age-related changes in mesenchymal stem cells identified using multi-omics approach ", European Cells and Materials 31:136-159, 2016.
GenBank Accession AAA52614.1, Nov. 8, 1994.
GenBank: CAA70214.1. "grp78 Homologue, Partial [*Neurospora crassa*]", Jul. 25, 2016.
Wang et al. "HSPA5 gene encoding HSP70 chaperone B1P in the endoplasmic reticulum", Gene 618:14-23, 2017.
NCBI Reference Sequence: XP_01 6339949.1, "Predicted: 78 kDa Glucose-regulated Protein Isoform X1 [*Sinocyclocheilus anshuiensis*]", May 3, 2016.
NCBI Reference Sequence: XP_004088869.1 "Predicted: 78 kDa Glucose-regulated Protein Isoform X1 [*Nomascus leucogenys*]", May 13, 2015.
Hitzeman, et al, J Biol Chem, 255:12073-12080, 1980.
Oakley, et al., Anal. Biochem. 1980, 105:361-363.
Zheng, Y.-Z. et al., "The Endoplasmic Reticulum Stress Markers GRP78 and CHOP Predict Disease-free Survival and Responsiveness to Chemotherapy in Breast Cancer", Breast Cancer Research and Treatment, 2014, vol. 145, pp. 349-358.
Bellotti, C. et al., "Detection of Mesenchymal Stem Cells Senescence by Prelamin A Accumulation at the Nuclear Level", SpringerPlus, 2016, vol. 5, 1427, pp. 1-8.
Turinetto, V. et al., "Senescence in Human Mesenchymal Stem Cells: Functional Changes and Implications in Stem Cell-Based Therapy", International Journal of Molecular Sciences, 2016, vol. 17, 1164, pp. 1-18.
Proteins; Structures and Molecular Principles, WH Freeman and Co, NY, 1983.
Chemical Approaches to the Synthesis of Peptides and Proteins, Williams et al, Eds., CRC Press, Boca Raton Florida, 1997, p. 1-17.
Chemistry of peptide synthesis, N. Leo Benoiton, Taylor & Francis, 2005, CRC press, p. 140-143.
Maniatis, et al, Molecular Cloning; A laboratory Manual, Cold Spring Harbor laboratory, 1982, Molecular Cloning: A Laboratory Manual, Cold Spring Harbor Press, NY, Third(2000) Edition, 161-264.
Li, Z. et al., "Glucose regulated protein 78: A critical link between tumor microenvironment and cancer hallmarks", Biochimica et Biophyscica Acta, vol. 1826, 2012, 13-22.
Pfaffenbach, K. et al., "The critical role of GRP78 in pysiologic and pathologic stress", Curr. Opin. in Cell Biol., vol. 23, 2011, 150-156.
Styner, M. et al., "Mechanical Strain Downregulates C/EBPß in MSC and Decreases Endoplasmic Reticulum Stress", PLOS One, vol. 7, Issue 12, 2012, 1-8.
Suda, T. et al., "Metabolic Regulation of Hematopoietic Stem Cells in the Hypoxic Niche", Cell Stem Cell, vol. 9, 2011, 298-310.
Wey, S. et al., "Acute Inducible Ablation of GRP78 Reveals Its Role in Hematopoietic Stem Cell Survival, Lymphogenesis and Regulation of Stress Signaling", PLoS ONE, vol. 7, Iss. 6, 2012, 1-10.
Hughes, S. et al., "Probing the ATP Site of GRP78 with Nucleotide Triphosphate Analogs", PLOS ONE, DOI:10.1371/journal.pone.0154862, May 4, 2016, 1-17.
English Translation of Office Action dated Dec. 22, 2022 for the CN patent application No. 201880074387.11-7.

(56) References Cited

OTHER PUBLICATIONS

Fan, G. "Role of Heat Shock Proteins in Stem Cell Behavior", Progress in Molecular Bio., vol. 111, http://dx.doi.org/10.1016/B978-0-12-398459-3.00014-9, 2012, 305-322.

* cited by examiner

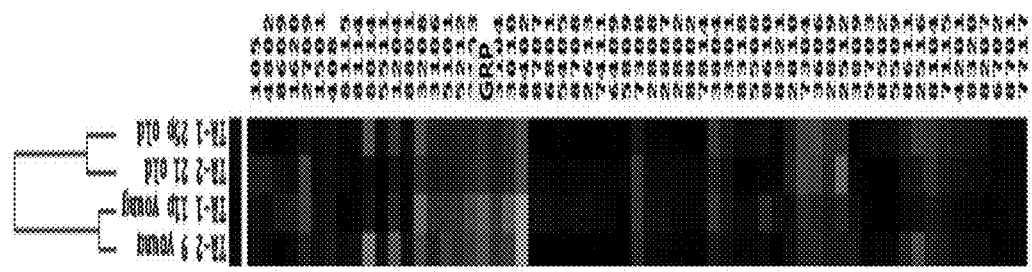
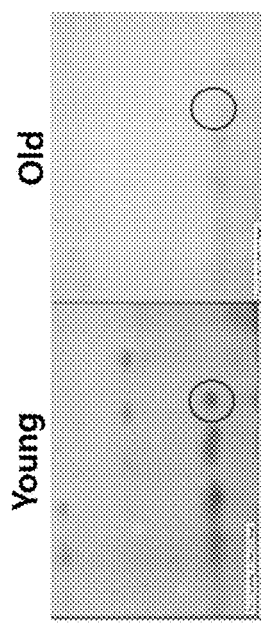
[Fig. 1]

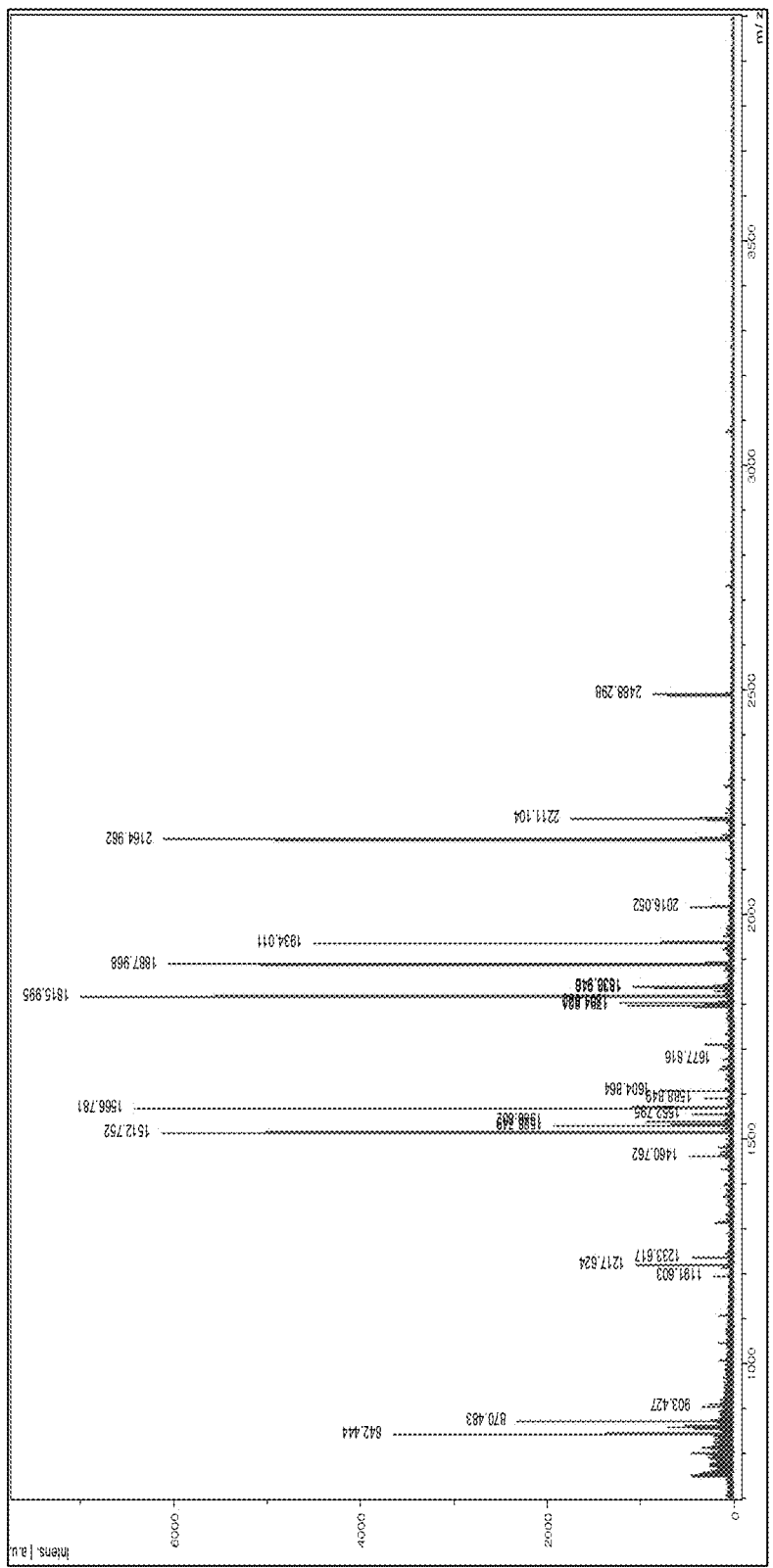
[Fig. 2]

1-32 Wild-type recognition site (WT): MEHRTRSWALGLSILGFFALLFSAGFVQQAHA (SEQ ID NO: 1)
1-32 Variant recognition site (K01): MEHRNRSWALGLSILGFFALLFSAGFVQQAHA (SEQ ID NO: 2)
1-32 Variant recognition site (K02): MDHRNRSWALGLSILGFFALLFSAGFVQQAHA (SEQ ID NO: 3)

[Fig. 3]

139-152 TFAPEEISAMVLTK (SEQ ID NO: 4)
186-197 DAGTIAGLNVMR (SEQ ID NO: 5)
325-336 AKFEELNMDLFR (SEQ ID NO: 6)

[Fig. 4]

KPYIQVDIGGQTKTFAPEEISA (SEQ ID NO: 7)
MVLTKMKETAEAYLGKKVTH (SEQ ID NO: 8)
AVVTVPAYFNDAQRQAT (SEQ ID NO: 9)
KDAGTIAGLNVMRIINEPTAAA (SEQ ID NO: 10)
IAYGLDKREGEKNILVFDLGGG (SEQ ID NO: 11)
TFDVSLLTIDNGVFEV (SEQ ID NO: 12)
VATNGDTHLGGEDFDQRV (SEQ ID NO: 13)
MEHFIKLYKKKTGKDVRK (SEQ ID NO: 14)

[Fig. 5]

CPLTLGIETVGGVMTKLIPR (SEQ ID NO: 15)
NTVVPTKKSQIFSTASDNQP (SEQ ID NO: 16)
TVTIKVYEGERPLTKDNHLL (SEQ ID NO: 17)
GTFDLTGIPPAPRGVPQIEVT (SEQ ID NO: 18)

[Fig. 6]

GRP78-DERIVED PEPTIDE FOR IDENTIFYING HIGH-EFFICIENCY STEM CELLS

RELATED APPLICATIONS

This application is a US national stage entry of International Application No. PCT/KR2018/012118, filed Oct. 15, 2018, which claims priority to Korean Application No. 10-2017-0133614, filed Oct. 13, 2017. The entire teachings of the above applications are incorporated herein by reference.

TECHNICAL FIELD

The present invention relates to a GRP78-derived peptide for screening highly efficient stem cells and the use thereof, and more particularly, to screening highly efficient stem cells using, as a marker, a GRP78-derived peptide capable of binding to the binding domain of GRP78 protein on the cell surface.

BACKGROUND ART

In recent years, various studies have been conducted on the possibility of using stem cells as cell therapy by differentiating stem cells, such as embryonic stem cells and adult stem cells, into various cells. Multipotent embryonic stem cells have attracted attention as cell therapy products due to their ability to differentiate into various cells. However, the use of embryonic stem cells poses ethical problems, and hence it is difficult to use these embryonic stem cells as cell therapy in practice. To avoid such ethical problems, studies on the use of adult stem cells have been actively conducted (*Trends in Neurosciences* 23:450, 2000).

Although adult stem cells have disadvantages in that when these cells are transplanted into other persons, they carry the risk of infection and have a relatively low differentiation potential, these cells have advantages in that they can be obtained in large numbers and are very safe for medical applications. Specifically, even when these cells are transplanted into the body for organ regeneration, they do not cause cancer, and do not cause immune rejection because they have originated from the adult body. Thus, these adult stem cells can be used for autologous transplantation. In addition, adult stem cells have site-specific differentiation potential according to the characteristics of surrounding tissue, and do not cause cancer even when they are injected in an undifferentiated state. Thus, these adult stem cells advantageously have the potential to produce necessary cells immediately after transplantation and also have self-renewal potential to create and store undifferentiated stem cells, if necessary (*JACC: Basic to Translational Science* 2:702-716, 2017).

During development of stem cells into a cell therapy product, a process of culturing isolated stem cells for a long period of time is essential in order to obtain the number of cells required to have an optimal therapeutic effect. Due to the long-term culture, development of the cell therapy product is inevitably performed in a state in which a large number of old cells is mixed or cells at various passages are mixed. This can cause problems in the stability and effectiveness of the stem cell therapy product, as well as quality control (*European Cells and Materials* 31:136-159, 2016). Therefore, in order to develop a cell therapy product using adult stem cells, a process of screening old cells mixed due to long-term culture is necessary. Although various efforts have, in fact, been made to control the quality of stem cell therapy products, established clear markers are still insufficient.

Meanwhile, GRP78 is an HSP 70 family chaperone protein that is present in the ER lumen. GRP78 is an important factor in protein transport/transfer into the ER and is a functional protein that is a key to maintaining intracellular calcium homeostasis. This protein consists of two domains connected to each other: one is a nucleotide-binding domain (NBD) that binds and degrades nucleotides in the ER, more specifically ATP, and the other is a substrate-binding domain (SBD) that binds to metabolic enzymes such as ATPase, as well as metabolism-related proteins and metabolic substrates (e.g., ADP) (*Gene* 618:14-23, 2017). These domains regulate energy metabolism and calcium metabolism inside and outside the ER while degrading ATP depending on intracellular calcium and ATP concentrations during metabolism.

Accordingly, the present inventors have made extensive efforts to find markers which may be used to remove old stem cells and screen only highly efficient stem cells, and as a result, have found that the protein GRP78 associated with glucose metabolism can be used as a senescence-associated stem cell marker as the number of passages increases during long-term culture of adult stem cells, and also found that the effect of the GRP78 protein can be enhanced by introducing the GRP78 protein into cells, thereby completing the present invention.

The above information disclosed in this Background section is only for enhancement of understanding of the background of the present invention. Therefore, it may not contain information that forms a conventional art that is already known in the art to which the present invention pertains.

SUMMARY OF THE INVENTION

An object of the present invention is to provide a peptide comprising a specific amino acid sequence capable of recognizing highly efficient stem cells, or a peptide capable of enhancing the effect of GRP78 protein, among the amino acid sequences of the marker GRP78 for developing a cell therapy product using adult stem cells and controlling the quality of the cell therapy product.

Another object of the present invention is to provide a method of screening highly efficient stem cells using the peptide or a method of increasing the efficiency of stem cells using the peptide to produce a stem cell therapy product having excellent efficacy.

To achieve the above objects, the present invention provides a peptide for screening highly efficient stem cells or increasing the efficiency of stem cells, the peptide being represented by an amino acid sequence selected from the group consisting of SEQ ID NOs: 1 to 18.

The present invention also provides a method of screening highly efficient stem cells using the peptide.

The present invention also provides a composition for screening highly efficient stem cells comprising the peptide.

The present invention also provides a kit for screening highly efficient stem cells comprising the peptide.

The present invention also provides a method of increasing the efficiency of stem cells by treating the stem cells with the peptide.

The present invention also provides a composition for increasing the efficiency of stem cells comprising the peptide.

BRIEF DESCRIPTION OF DRAWINGS

FIG. 1 is a list of proteins showing significant changes as a result of proteomic analysis performed on young cells and old cells.

FIG. 2 shows the peptide peaks identified by MALDI-TOF-TOF analysis of GRP78 protein which showed a tendency to significantly decrease in old cells.

FIG. 3 shows a wild-type peptide sequence, identified as a GRP78 recognition site by MALDI-TOF-TOF analysis, and variant peptide sequences thereof.

FIG. 4 shows peptide sequences identified as having phosphorylation and oxidation potentials among the full-length sequence of GRP78 protein by protein structure analysis and sequencing.

FIG. 5 shows peptide sequences that bind to nucleotides in the nucleus, among GRP78-derived peptides.

FIG. 6 shows peptide sequences that bind to other substrates, among GRP78-derived peptides.

DETAILED DESCRIPTION AND PREFERRED EMBODIMENTS OF THE INVENTION

Unless otherwise defined, all the technical and scientific terms used in the present specification have the same meanings as commonly understood by those skilled in the art to which the present disclosure pertains. In general, the nomenclature used in the present specification is well known and commonly used in the art.

In the present invention, GRP78 (glucose-regulated protein 78) showing a significant expression change in old stem cells was identified by examining proteomic changes as senescence of adult stem cells progressed. It was confirmed that the expressions of GRP78 gene and protein in old stem cells significantly decreased compared to those in young highly efficient stem cells. Accordingly, the amino acid sequence of the GRP78 protein was analyzed by MALDI-TOF/TOF and a wild-type peptide sequence identified as a GRP78 recognition site and variant peptide sequence were obtained. Also, protein structure analysis and sequencing were performed and peptide sequences having phosphorylation and oxidation potentials among the full-length sequence of the GRP78 protein were obtained. In addition, using endoplasmic reticulum chaperone BiP protein, peptides for GRP78 screening, which bind to nucleotides in the nucleus, and peptides for GRP78 screening, which bind to other substrates, were synthesized.

The GRP78-derived peptide of the present invention can serve as a cell surface marker that binds to the binding domain of the GRP78 protein on the cell surface, thereby screening cells labeling GRP78. In addition, the effect of the GRP78 protein can be increased by treating cells, which have decreased expression of the GRP78 protein, with the GRP78-derived peptide, or introducing the GRP78-derived peptide into the cells.

Therefore, one aspect of the present invention is directed to a peptide for screening highly efficient stem cells or enhancing the efficiency of stem cells, the peptide being represented by an amino acid sequence selected from the group consisting of SEQ ID NOs: 1 to 18.

In the present invention, the peptide may be derived from GRP78.

The nucleotide sequence and amino acid sequence of GRP78 of the present invention may be obtained from a known database such as NCBI's GenBank (e.g., GenBank Accession AAA52614.1).

In the present invention, the peptides represented by the amino acid sequences of SEQ ID NOs: 1 to 3 may recognize the 1-32 site of GRP78, and may be the 1-32 wild-type recognition site (WT): MEHRTRSWALGLSILGFFALLF-SAGFVQQAHA (SEQ ID NO: 1), the 1-32 variant recognition site (KO1): MEHRNRSWALGLSILGFFALLF-SAGFVQQAHA (SEQ ID NO: 2), and the 1-32 variant recognition site (KO2): MDHRNRSWALGLSILGFFALL-FSAGFVQQAHA (SEQ ID NO: 3).

In the present invention, the peptides represented by the amino acid sequences of SEQ ID NOs: 4 to 6 preferably recognize the phosphorylation or oxidation site of the GRP78 protein, and may more preferably be 139-152 TFAP-EEISAMVLTK (SEQ ID NO: 4), 186-197 DAGTI-AGLNVMR (SEQ ID NO: 5), and 325-336 AKFEELNMDLFR (SEQ ID NO: 6).

In the present invention, the peptides represented by the amino acid sequences of SEQ ID NOs: 7 to 14 may be the 125-280 site of GRP78, may preferably recognize ATP in the nucleus, which is regulated by GRP78, and may more preferably be

KPYIQVDIGGGQTKTFAPEEISA, (SEQ ID NO: 7)

MVLTKMKETAEAYLGKKVTH, (SEQ ID NO: 8)

AVVTVPAYFNDAQRQAT, (SEQ ID NO: 9)

KDAGTIAGLNVMRIINEPTAAA, (SEQ ID NO: 10)

IAYGLDKREGEKNILVFDLGGG, (SEQ ID NO: 11)

TFDVSLLTIDNGVFEV, (SEQ ID NO: 12)

VATNGDTHLGGEDFDQRV, (SEQ ID NO: 13)
and

MEHFIKLYKKKTGKDVRK. (SEQ ID NO: 14)

Since GRP78 regulates homeostasis of ATP and calcium in the endoplasmic reticulum (ER) and ATP is a nucleotide, the peptides represented by the amino acid sequences of SEQ ID NOs: 7 to 14 are preferably peptides having a nucleotide-binding domain (NBD), and can increase the efficiency of stem cells by regulating the homeostasis of ATP and calcium in the ER.

In the present invention, the peptides represented by the amino acid sequences of SEQ ID NOs: 15 to 18 may be the 420-500 site of GRP78, preferably recognize other substrates that are ATP degradation products in the nucleus, which are regulated by GRP78, and may more preferably be CPLTLGIETVGGVMTKLIPR (SEQ ID NO: 15), NTVVPTKKSQIFSTASDNQP (SEQ ID NO: 16), TVTIKVYEGERPLTKDNHLL (SEQ ID NO: 17), and GTFDLTGIPPAPRGVPQIEVT (SEQ ID NO: 18).

Since GRP78 regulates homeostasis of ATP and calcium in the endoplasmic reticulum (ER) and stimulates ATP degradation, the peptides represented by the amino acid sequences of SEQ ID NOs: 15 to 18 are preferably peptides having a substrate-binding domain (SBD), and may bind to a substrate so as to be able to bind to ATP itselfs, thereby increasing the efficiency of stem cells.

The peptide of the present invention may be used to screen stem cells expressing the GRP78 protein on the cell surface. In addition, the peptide of the present invention may be introduced into the cytoplasm of stem cells in which intracellular expression of the GRP78 protein decreased due to senescence or external stimulation, thereby screening highly efficient stem cells and increasing stemness.

The peptide of the present invention may be easily produced by chemical synthesis methods known in the art (Creighton, Proteins; Structures and Molecular Principles, W H Freeman and Co, NY, 1983). Typical methods include, but are not limited to, liquid or solid phase synthesis, fragment condensation, and F-MOC or T-BOC chemistry (Chemical Approaches to the Synthesis of Peptides and Proteins, Williams et al, Eds., CRC Press, Boca Raton Fla., 1997; Chemistry of peptide synthesis, N. Leo Benoiton, Taylor & Francis, 2005, CRC press, page 140-143).

In addition, the peptide of the present invention may be produced by genetic engineering methods. First, a DNA sequence encoding the peptide is constructed according to a conventional method. The DNA sequence may be constructed by PCR amplification using suitable primers. Alternatively, the DNA sequence may also be synthesized by a standard method known in the art, for example, an automated DNA synthesizer (e.g., commercially available from Biosearch or Applied Biosystems). The constructed DNA sequence is inserted into a vector comprising one or more expression control sequences (for example, promoters, enhancers, etc.), which are operatively linked to the DNA sequence and regulate the expression of the DNA sequence, and a host cell is transformed with the resulting recombinant expression vector. The resulting transformant is cultured in suitable medium under suitable culture conditions so that the DNA sequence is expressed, and then a substantially pure peptide encoded by the DNA sequence is recovered from the cell culture. The recovery of peptide may be carried out by a conventional method known in the art (for example, chromatography). As used herein, the term "substantially pure peptide" means that the peptide according to the present invention is substantially free from any other proteins derived from the host. The genetic engineering method for synthesis of the peptide of the present invention can be found in the following literature: Maniatis et al, Molecular Cloning; A laboratory Manual, Cold Spring Harbor laboratory, 1982; Sambrook et al, Molecular Cloning: A Laboratory Manual, Cold Spring Harbor Press, NY, Second (1998) and Third (2000) Edition; and Hitzeman et al, J Biol Chem, 255:12073-12080, 1990. In the present invention, the highly efficient stem cells may express GRP78. In the present invention, the highly efficient stem cells may be non-senescent young stem cells.

In the present invention, the stem cells are preferably adult stem cells, but are not limited thereto.

As used herein, the term "stem cells" refers to pluripotent cells capable of differentiating into endodermal, mesodermal and ectodermal cells in animals, or multipotent cells capable of differentiating into closely related cells in tissues or functions. The term refers to a cell capable of dividing into two or more new cells while having self-renewal ability, and the stem cells may be classified into totipotent stem cells, pluripotent stem cells, and multipotent stem cells.

As used herein, the term "adult stem cells" refers to multipotent cells obtained by isolating stem cells from each tissue and culturing the isolated stem cells in vitro, and includes bone marrow stem cells, retinal stem cells, retinal Muller glial cells, neural stem cells, and the like. The stem cells may be derived from mammals, including humans and primates, as well as livestock such as cattle, pigs, sheep, horses, dogs, rats, rats, and cats. Preferably, the stem cells may be derived from humans.

As used herein, the term "senescence" means that the differentiation or proliferation potential of adult stem cells decreases due to an increase in the age of an individual or an increase in the number of passages.

As used herein, the term "passage" means replacing a culture vessel or dividing and culturing a cell population, in a method in which a portion of cells are periodically transferred to a fresh culture vessel in order to continuously culture the cells in a healthy state for a long period of time, and then the cells are continuously subcultured while the culture medium is replaced. One passage refers to replacing the culture vessel once or dividing and culturing the cell population. In the present invention, low-passage or young-passage stem cells may refer to stem cells having a high differentiation ability or therapeutic effect, and high-passage or old-passage stem cells may refer to stem cells having a low differentiation ability or therapeutic effect, but are not limited thereto.

In the present invention, the young passage may have a passage number of 0 to 3, preferably 0 to 2. In addition, the old passage may have a passage number of 15 to 25, preferably 20 to 25.

In the present invention, the young stem cells may have a passage number of 0 to 3, preferably 0 to 2. In addition, the old stem cells may have a passage number of 15 to 25, preferably 20 to 25.

That is, the "old stem cells" in the present invention refers to stem cells in which the differentiation or proliferation ability of adult stem cells has decreased due to an increase in the number of passages, and the "highly efficient stem cells" refers to stem cells that have excellent efficacy as cell therapy products because the adult stem cells therein have a very high differentiation or proliferation ability. In other words, the "highly efficient stem cells" refers to those that exhibit the differentiation or proliferation potential equivalent to young-passage stem cells.

Another aspect of the present invention is directed to a method of screening highly efficient stem cells using a peptide represented by an amino acid sequence selected from the group consisting of SEQ ID NOs: 1 to 18.

In the present invention, the method may comprise steps of: (a) conjugating a fluorescent to a peptide specific for GRP78; (b) binding the fluorescent-conjugated peptide to stem cells; and (c) screening GRP78-expressing stem cells under a fluorescence microscope.

Still another aspect of the present invention is directed to a composition for screening highly efficient stem cells, the composition comprising a peptide represented by an amino acid sequence selected from the group consisting of SEQ ID NOs: 1 to 18.

Yet another aspect of the present invention is directed to a kit for screening highly efficient stem cells, the kit comprising a peptide represented by an amino acid sequence selected from the group consisting of SEQ ID NOs: 1 to 18. In the present invention, the kit may be an RT-PCR kit, a DNA chip kit or a protein chip kit.

The kit of the present invention may be a diagnostic kit composed of one or more compositions, solutions or instruments, which are suitable for analysis methods, and may be an RT-PCR kit, a DNA chip kit or a protein chip kit. The RT-PCR kit may comprise, in addition to each primer pair specific for the marker gene, a test tube or another suitable container, a reaction buffer, deoxynucleotides (dNTPs), enzymes such as Taq-polymerase, reverse transcriptase and DNase, an RNase inhibitor, DEPC-water, sterile water, etc. Also, it may comprise a primer pair specific to a gene which is used as a quantitative control. The DNA chip kit may comprise a substrate in which cDNA corresponding to the gene or a fragment thereof is attached as a probe. The substrate may contain cDNA corresponding to a quantification control gene or a fragment thereof.

In addition, the kit according to the present invention may be a diagnostic kit comprising an agent for measuring the protein level, in which the agent for measuring the protein level is preferably an antibody specific for the protein. Thus, the kit comprising the agent for measuring the protein level may be a kit for detection of markers, which comprises essential elements required for carrying out, for example, ELISA. This kit may also comprise reagents that may detect antibodies forming "antigen-antibody complexes", for example, labeled secondary antibodies, chromophores, enzymes (e.g., conjugated with antibodies) and their substrates. Also, it may comprise an antibody specific to a control protein for quantification.

Furthermore, the amount of antigen-antibody complexes formed may be quantitatively determined by measuring the signal intensity of a detection label. Such a detection label may be selected from the group consisting of, but not necessarily limited to, enzymes, fluorescent substances, ligands, luminescent substances, microparticles, redox molecules and radioactive isotopes.

Methods for measuring protein levels include, but not necessarily limited to, Western blotting, ELISA, radioimmunoassay, radioimmunodiffusion, Ouchterlony immunodiffusion assay, rocket immunoelectrophoresis assay, immunohistostaining assay, immunoprecipitation assay, complement fixation assay, fluorescence activated cell sorter (FACS), protein chip assay, etc., and the protein level may be measured using methods known to those skilled in the art.

Yet another aspect of the present invention is directed to a method of increasing the efficiency of stem cells by treating the stem cells with a peptide represented by an amino acid selected from the group consisting of SEQ ID NOs: 1 to 18, or introducing the peptide into the stem cell.

In the present invention, the stem cells having increased efficiency may express GRP78.

In the present invention, the stem cells are preferably adult stem cells, but are not limited thereto.

As used herein, the term "stem cells" refers to pluripotent cells capable of differentiating into endodermal, mesodermal and ectodermal cells in animals, or multipotent cells capable of differentiating into closely related cells in tissues or functions. The term refers to a cell capable of dividing into two or more new cells while having self-renewal ability, and the stem cells may be classified into totipotent stem cells, pluripotent stem cells, and multipotent stem cells.

As used herein, the term "adult stem cells" refers to multipotent cells obtained by isolating stem cells from each tissue and culturing the isolated stem cells in vitro, and includes bone marrow stem cells, retinal stem cells, retinal Muller glial cells, neural stem cells, and the like. The stem cells may be derived from mammals, including humans and primates, as well as livestock such as cattle, pigs, sheep, horses, dogs, mouse, rats, and cats. Preferably, the stem cells may be derived from humans.

As used herein, the term "increasing the efficiency" of stem cells means that the differentiation or proliferation potential of adult stem cells increases. The term "highly efficient stem cells" or "stem cells having increased efficiency" refers to those that exhibit the differentiation or proliferation potential equivalent to young-passage stem cells.

In the present invention, "treating with the peptide" or "introducing the peptide into" may be performed by treating a cell culture medium directly with the peptide or treating the cell culture medium with a mixture of the peptide and a biomaterial for culture, and the biomaterial refers to a synthetic polymer or a natural polymer.

In the present invention, the synthetic polymer is preferably selected from among poloxamer, polyethylene glycol and polypropylene glycol, and the natural polymer is preferably selected from among vitronectin, collagen, gelatin, alginic acid, chondroitin sulfate, fibronectin and extracellular matrix protein, but the scope of the present invention is not limited thereto.

Yet another aspect of the present invention is directed to a composition for increasing efficiency of stem cells, the composition comprising a peptide represented by an amino acid sequence selected from the group consisting of SEQ ID NOs: 1 to 18.

EXAMPLES

Hereinafter, the present invention will be described in more detail with reference to examples. It will be obvious to skilled in the art that these examples are merely to illustrate the present invention, and the scope of the present invention is not limited by these examples.

Example 1: Change and Identification of GRP78 Protein by Proteomic Analysis

In order to examine the changes in proteomics with the progress of senescence of adult stem cells, proteomic analysis was performed using each cell pellet cultured at each passage.

(1) Protein Extraction (Protein Sample Preparation)

Protein extraction from a sample was performed as follows. A 2DE lysis solution composed of 7M urea, 2M thiourea, 4% (w/v) 3-[(3-cholamidopropyl)dimethylammonio]-1-propanesulfonate (CHAPS), 1% (w/v) dithiothreitol (DTT), 2% (v/v) Pharmalyte and 1 mM benzamidine was added to the sample. For protein extraction, the mixture was vortexed for 1 hour and centrifuged at 12,000 rpm and 25° C. for 1 hour. The supernatant was used as a sample for two-dimensional electrophoresis. Measurement of protein concentration was performed by the Bradford method.

(2) 2D Electrophoresis

For primary isoelectric focusing (IEF), IPG strips were reswollen in a reswelling buffer (containing 7M urea, 2M thiourea, 2% 3-[(3-cholamidopropy)dimethyammonio]-1-propanesulfonate (CHAPS), 1% dithiothreitol (DTT), and 1% Pharmalyte) at room temperature for about 12 to 16 hours. 100 μg of the sample per strip was used, and IEF was performed at 20° C. using the Multiphore II system (Amersham Biosciences) according to the manufacturer's manual. For IEF, the voltage was increased from 150V to 3,500V within 3 hours and maintained at 3,500V for 26 hours, and IEF was completed at 96 kVh.

Before SDS-PAGE was performed, IPG strips were incubated in a 1% DTT-containing equilibration buffer (50 mM Tris-Cl, pH 6.8, 6M urea, 2% SDS, and 30% glycerol) for 10 minutes, and immediately further incubated in a 2.5% iodoacetamide-containing equilibration buffer for 10 minutes. Equilibrated strips were arranged on SDS-PAGE gels (20× 24 cm, 10 to 16%), and run at 1.7 kVh and 20° C. using a Hoefer DALT 2D system. After 2D electrophoresis was completed, proteins on the 2D gels were visualized by silver staining according to the method described in Oakley et al., Anal. Biochem. 1980, 105:361-363, and a glutaraldehyde treatment step was omitted for protein identification by mass spectrometry. The silver-stained 2D gel was scanned, and stored as a TIFF file.

(3) Image Analysis

Quantitative analysis for examining changes in expression of protein spots from the scanned image was performed using PDQuest software (version 7.0, BioRad). The quantity of each spot was normalized by the total valid spot intensity, and protein spots showing at least 2-fold significant changes in expression compared to control were selected.

Example 2: Amino Acid Sequencing of GRP78 Protein Obtained by MALDI-TOF/TOF Analysis The protein spot selected in the 2DE analysis was washed with 50% acetonitrile, dried under vacuum, and then subjected to in-gel digestion with trypsin. The degraded sample was analyzed using a BRUKER AUTOFLEX SPEED with LIFT™ ion optics. The results of the mass spectrometry sequencing of the peptide were provided in the MASCOT search form (FIG. 2).

Example 3: GRP78-Specific Recognition Related Sequences

FIG. 3 shows a wild-type peptide sequence, identified as a GRP78 recognition site by MALDI-TOF-TOF analysis, and variant peptide sequences thereof, developed by the present inventors.

```
1-32 wild-type recognition site (WT):
                                    (SEQ ID NO: 1)
MEHRTRSWALGLSILGFFALLFSAGFVQQAHA 1-32 variant recognition site (KO1):
                                    (SEQ ID NO: 2)
MEHRNRSWALGLSILGFFALLFSAGFVQQAHA 1-32 variant recognition site (KO2):
                                    (SEQ ID NO: 3)
MDHRNRSWALGLSILGFFALLFSAGFVQQAHA
```

The sequence consisting of $1^{st}$ to $32^{nd}$ amino acids of the GRP78 protein was selected as a wild-type sequence, and variant sequences were selected.

Example 4: Phosphorylation Sequence

FIG. 4 shows peptide sequences identified as having phosphorylation and oxidation potentials among the full-length sequence of GRP78 protein by protein structure analysis and sequencing. In this Example, sites predicted to have the binding domain or a major functional domain in the GRP78 protein were selected and synthesized.

```
                                    (SEQ ID NO: 4)
139-152 TFAPEEISAMVLTK (SEQ ID NO: 5)
186-197 DAGTIAGLNVMR (SEQ ID NO: 6)
325-336 AKFEELNMDLFR
```

Example 5: GRP78 Peptide Synthesis

To synthesize peptides for GRP78 screening, the endoplasmic reticulum chaperone BiP protein [*Homo sapiens*] (NP_005338.1) (SEQ ID NO: 19), which consists of 654 amino acids, was used. In addition to this sequence, various sequences including the GRP78 binding domain WIFP-WIQL (SEQ ID NO: 20) may be used. Other detailed information is available from uniprot.org/uniprot/P11021.

Peptides for GRP78 screening were synthesized in large amounts using a peptide synthesizer (Apex 396, AAPPTec, Louisville, Ky., USA). The synthesized peptides were purified by reverse phase high-performance chromatography (HPLC) using a Vydac C18 column and a 0.1% TFA-containing water/acetonitrile gradient. The synthesized peptides having a purity of 98% or higher were used. The synthesized peptides were freeze-dried, and then stored in dark at −80° C. until use.

(1) Peptides that Bind to Nucleotides in Nucleus

To synthesize peptides for GRP78 screening that bind to nucleotides in the nucleus, nucleotide or amino acid sequences containing the 125-280 sequence of GRP78, or those containing the following sequences were selected.

As a protein in the structure of GRP78, NBD (nucleotide binding domain) is divided into two large spherical domains (I and II), and each of the domains is subdivided into subdomains A and B. That is, NBD is divided into IA, IB, IIA and IIB sequences. SEQ ID NOs: 7 and 8 contain IA, SEQ ID NOs: 9 and 10 contain IB, SEQ ID NOs: 11 and 12 contains IIA, and SEQ ID NOs: 13 and 14 contain IIB. The peptides recognize and bind to ATP (nucleotide) which is regulated by GRP78 in cells.

The eight sequences are as follows and are also shown in FIG. 5.

```
                                    (SEQ ID NO: 7)
KPYIQVDIGGGQTKTFAPEEISA (SEQ ID NO: 8)
MVLTKMKETAEAYLGKKVTH (SEQ ID NO: 9)
AVVTVPAYFNDAQRQAT (SEQ ID NO: 10)
KDAGTIAGLNVMRIINEPTAAA (SEQ ID NO: 11)
IAYGLDKREGEKNILVFDLGGG (SEQ ID NO: 12)
TFDVSLLTIDNGVFEV (SEQ ID NO: 13)
VATNGDTHLGGEDFDQRV (SEQ ID NO: 14)
MEHFIKLYKKKTGKDVRK
```

The peptides of SEQ ID NOs: 7 and 8 were synthesized starting from the N-terminus by F-moc solid phase peptide synthesis. The synthesized peptide sequences were cut from resin, washed, freeze-dried, and then separated and purified by liquid chromatography. The molecular weights of the purified peptides were analyzed by MALDI-TOF analysis.

(2) Peptides that Bind to Other Substrates

To synthesize peptides for GRP78 screening that bind to other substrates, sequences containing the 420-500 sequence of GRP78 or those containing the following sequences were selected.

After ATP binds to the NBD of GRP78 during ATP degradation, a change in the structure of the SBD (substrate binding domain) of the GRP78 sequence occurs to promote the degradation process occurring in the NBD. The SBD is divided into two domains: SBD alpha, and SBD beta. The two domains are represented by SEQ ID NOs: 15 and 16, and SEQ ID NOs: 17 and 18, respectively. These peptides bind to substrates that bind to degradation products produced by the degradation of ATP that is regulated by GRP78. These peptides may further promote the degradation process.

The four sequences are as follows and are shown in FIG. 6.

```
                                     (SEQ ID NO: 15)
        CPLTLGIETVGGVMTKLIPR (SEQ ID NO: 16)
        NTVVPTKKSQIFSTASDNQP (SEQ ID NO: 17)
        TVTIKVYEGERPLTKDNHLL (SEQ ID NO: 18)
        GTFDLTGIPPAPRGVPQIEVT
```

The peptides of SEQ ID NOs: 15 to 18 were synthesized by F-moc solid phase peptide synthesis. The synthesized peptide sequences were cut from resin, washed, freeze-dried, and then separated and purified by liquid chromatography. The molecular weights of the purified peptides were analyzed by MALDI-TOF analysis.

Example 6: Screening of Stem Cells Using Synthetic GRP78 Peptides

To screen highly efficient stem cells using the peptides synthesized in Examples 3 to 5, fluorescent-labeled GRP78 peptides were used. That is, cells expressing GRP78 on the cell surface were screened. Alternatively, the GRP78 protein in the nucleus or other intracellular organelle was labeled with fluorescent to distinguish the GRP78 labeled in the nucleus from the one in the membrane. The cell permeability and change in intracellular distribution of each of the peptides were evaluated.

To evaluate the cell permeability of each of the fluorescent-labeled peptides, cells were cultured in a 12-well plate in a 5% $CO_2$ humidified chamber at 37° C. and attached, and then the culture medium was removed. Each of the peptides was added to the cells at an optimal concentration, and control cells were treated with PBS. After culturing in a 5% $CO_2$ humidified chamber at 37° C. for 2 hours and 8 hours, the cells were carefully washed three times with PBS, and were incubated with DAPI for 30 minutes, and the distribution of the peptide in the nucleus was observed. After incubation, the cells were washed twice with PBS and analyzed by fluorescence imaging with a fluorescence microscope (OLYMPUS IX-70).

INDUSTRIAL APPLICABILITY

According to the present invention, the GRP78-derived peptide comprising only a specific amino acid sequence capable of recognizing highly efficient stem cells, among the amino acid sequence of GRP78, makes it possible to screen only non-senescent young stem cells. In addition, when stem cells are treated with the GRP78-derived peptide or the GRP78-derived peptide is introduced into stem cells, the efficiency of the stem cells can be increased. Thus, the GRP78-derived peptide is useful for the production of stem cell therapy products having excellent efficacy.

Although the present invention has been described in detail with reference to specific features, it will be apparent to those skilled in the art that this description is only of a preferred embodiment thereof, and does not limit the scope of the present invention. Thus, the substantial scope of the present invention will be defined by the appended claims and equivalents thereto.

---

The invention claimed is:

1. A peptide consisting of the amino acid sequence of SEQ ID NO: 14.

2. The peptide of claim 1, wherein the peptide is derived from Glucose-regulated protein 78 (GRP78).

3. The peptide of claim 1, wherein the peptide of SEQ ID NO: 14 binds ATP, which is regulated by GRP78.

4. A method of screening highly efficient stem cells that express GRP78, comprising steps of:
   (a) conjugating a fluorescent label to a peptide that binds GRP78 and consists of the amino acid sequence of SEQ ID NO: 14;
   (b) culturing the fluorescent labeled-conjugated peptide with stem cells to allow binding of the fluorescent labeled-conjugated peptide with stem cells that express GRP78; and
   (c) screening for GRP78-expressing stem cells under a fluorescence microscope.

5. A composition comprising the peptide of claim 1.

6. A kit comprising the peptide of claim 1.

7. A method of increasing efficiency of stem cells that express GRP78 comprising treating stem cells that express GRP78 with the peptide of claim 1.

* * * * *

SEQUENCE LISTING

```
<160> NUMBER OF SEQ ID NOS: 20

<210> SEQ ID NO 1
<211> LENGTH: 32
<212> TYPE: PRT
<213> ORGANISM: Artificial Sequence
<220> FEATURE:
<223> OTHER INFORMATION: GRP78

<400> SEQUENCE: 1

Met Glu His Arg Thr Arg Ser Trp Ala Leu Gly Leu Ser Ile Leu Gly
1               5                   10                  15

Phe Phe Ala Leu Leu Phe Ser Ala Gly Phe Val Gln Gln Ala His Ala
                20                  25                  30

<210> SEQ ID NO 2
<211> LENGTH: 32
<212> TYPE: PRT
<213> ORGANISM: Artificial Sequence
<220> FEATURE:
<223> OTHER INFORMATION: GRP78

<400> SEQUENCE: 2

Met Glu His Arg Asn Arg Ser Trp Ala Leu Gly Leu Ser Ile Leu Gly
1               5                   10                  15
```

```
Phe Phe Ala Leu Leu Phe Ser Ala Gly Phe Val Gln Gln Ala His Ala
            20                  25                  30

<210> SEQ ID NO 3
<211> LENGTH: 32
<212> TYPE: PRT
<213> ORGANISM: Artificial Sequence
<220> FEATURE:
<223> OTHER INFORMATION: GRP78

<400> SEQUENCE: 3

Met Asp His Arg Asn Arg Ser Trp Ala Leu Gly Leu Ser Ile Leu Gly
1               5                   10                  15

Phe Phe Ala Leu Leu Phe Ser Ala Gly Phe Val Gln Gln Ala His Ala
            20                  25                  30

<210> SEQ ID NO 4
<211> LENGTH: 14
<212> TYPE: PRT
<213> ORGANISM: Artificial Sequence
<220> FEATURE:
<223> OTHER INFORMATION: GRP78

<400> SEQUENCE: 4

Thr Phe Ala Pro Glu Glu Ile Ser Ala Met Val Leu Thr Lys
1               5                   10

<210> SEQ ID NO 5
<211> LENGTH: 12
<212> TYPE: PRT
<213> ORGANISM: Artificial Sequence
<220> FEATURE:
<223> OTHER INFORMATION: GRP78

<400> SEQUENCE: 5

Asp Ala Gly Thr Ile Ala Gly Leu Asn Val Met Arg
1               5                   10

<210> SEQ ID NO 6
<211> LENGTH: 12
<212> TYPE: PRT
<213> ORGANISM: Artificial Sequence
<220> FEATURE:
<223> OTHER INFORMATION: GRP78

<400> SEQUENCE: 6

Ala Lys Phe Glu Glu Leu Asn Met Asp Leu Phe Arg
1               5                   10

<210> SEQ ID NO 7
<211> LENGTH: 23
<212> TYPE: PRT
<213> ORGANISM: Artificial Sequence
<220> FEATURE:
<223> OTHER INFORMATION: GRP78

<400> SEQUENCE: 7

Lys Pro Tyr Ile Gln Val Asp Ile Gly Gly Gly Gln Thr Lys Thr Phe
1               5                   10                  15

Ala Pro Glu Glu Ile Ser Ala
            20

<210> SEQ ID NO 8
<211> LENGTH: 20
<212> TYPE: PRT
```

```
<213> ORGANISM: Artificial Sequence
<220> FEATURE:
<223> OTHER INFORMATION: GRP78

<400> SEQUENCE: 8

Met Val Leu Thr Lys Met Lys Glu Thr Ala Glu Ala Tyr Leu Gly Lys
1               5                   10                  15

Lys Val Thr His
            20

<210> SEQ ID NO 9
<211> LENGTH: 17
<212> TYPE: PRT
<213> ORGANISM: Artificial Sequence
<220> FEATURE:
<223> OTHER INFORMATION: GRP78

<400> SEQUENCE: 9

Ala Val Val Thr Val Pro Ala Tyr Phe Asn Asp Ala Gln Arg Gln Ala
1               5                   10                  15

Thr

<210> SEQ ID NO 10
<211> LENGTH: 22
<212> TYPE: PRT
<213> ORGANISM: Artificial Sequence
<220> FEATURE:
<223> OTHER INFORMATION: GRP78

<400> SEQUENCE: 10

Lys Asp Ala Gly Thr Ile Ala Gly Leu Asn Val Met Arg Ile Ile Asn
1               5                   10                  15

Glu Pro Thr Ala Ala Ala
            20

<210> SEQ ID NO 11
<211> LENGTH: 22
<212> TYPE: PRT
<213> ORGANISM: Artificial Sequence
<220> FEATURE:
<223> OTHER INFORMATION: GRP78

<400> SEQUENCE: 11

Ile Ala Tyr Gly Leu Asp Lys Arg Glu Gly Glu Lys Asn Ile Leu Val
1               5                   10                  15

Phe Asp Leu Gly Gly Gly
            20

<210> SEQ ID NO 12
<211> LENGTH: 16
<212> TYPE: PRT
<213> ORGANISM: Artificial Sequence
<220> FEATURE:
<223> OTHER INFORMATION: GRP78

<400> SEQUENCE: 12

Thr Phe Asp Val Ser Leu Leu Thr Ile Asp Asn Gly Val Phe Glu Val
1               5                   10                  15

<210> SEQ ID NO 13
<211> LENGTH: 18
<212> TYPE: PRT
<213> ORGANISM: Artificial Sequence
<220> FEATURE:
<223> OTHER INFORMATION: GRP78
```

<400> SEQUENCE: 13

Val Ala Thr Asn Gly Asp Thr His Leu Gly Gly Glu Asp Phe Asp Gln
1               5                   10                  15

Arg Val

<210> SEQ ID NO 14
<211> LENGTH: 18
<212> TYPE: PRT
<213> ORGANISM: Artificial Sequence
<220> FEATURE:
<223> OTHER INFORMATION: GRP78

<400> SEQUENCE: 14

Met Glu His Phe Ile Lys Leu Tyr Lys Lys Thr Gly Lys Asp Val
1               5                   10                  15

Arg Lys

<210> SEQ ID NO 15
<211> LENGTH: 20
<212> TYPE: PRT
<213> ORGANISM: Artificial Sequence
<220> FEATURE:
<223> OTHER INFORMATION: GRP78

<400> SEQUENCE: 15

Cys Pro Leu Thr Leu Gly Ile Glu Thr Val Gly Gly Val Met Thr Lys
1               5                   10                  15

Leu Ile Pro Arg
            20

<210> SEQ ID NO 16
<211> LENGTH: 20
<212> TYPE: PRT
<213> ORGANISM: Artificial Sequence
<220> FEATURE:
<223> OTHER INFORMATION: GRP78

<400> SEQUENCE: 16

Asn Thr Val Val Pro Thr Lys Lys Ser Gln Ile Phe Ser Thr Ala Ser
1               5                   10                  15

Asp Asn Gln Pro
            20

<210> SEQ ID NO 17
<211> LENGTH: 20
<212> TYPE: PRT
<213> ORGANISM: Artificial Sequence
<220> FEATURE:
<223> OTHER INFORMATION: GRP78

<400> SEQUENCE: 17

Thr Val Thr Ile Lys Val Tyr Glu Gly Glu Arg Pro Leu Thr Lys Asp
1               5                   10                  15

Asn His Leu Leu
            20

<210> SEQ ID NO 18
<211> LENGTH: 21
<212> TYPE: PRT
<213> ORGANISM: Artificial Sequence
<220> FEATURE:
<223> OTHER INFORMATION: GRP78

```
<400> SEQUENCE: 18

Gly Thr Phe Asp Leu Thr Gly Ile Pro Pro Ala Pro Arg Gly Val Pro
1               5                   10                  15

Gln Ile Glu Val Thr
            20

<210> SEQ ID NO 19
<211> LENGTH: 654
<212> TYPE: PRT
<213> ORGANISM: Artificial Sequence
<220> FEATURE:
<223> OTHER INFORMATION: Endoplasmic reticulum chaperone BiP

<400> SEQUENCE: 19

Met Lys Leu Ser Leu Val Ala Ala Met Leu Leu Leu Ser Ala Ala
1               5                   10                  15

Arg Ala Glu Glu Glu Asp Lys Lys Glu Asp Val Gly Thr Val Val Gly
                20                  25                  30

Ile Asp Leu Gly Thr Thr Tyr Ser Cys Val Gly Val Phe Lys Asn Gly
            35                  40                  45

Arg Val Glu Ile Ile Ala Asn Asp Gln Gly Asn Arg Ile Thr Pro Ser
        50                  55                  60

Tyr Val Ala Phe Thr Pro Glu Gly Glu Arg Leu Ile Gly Asp Ala Ala
65                  70                  75                  80

Lys Asn Gln Leu Thr Ser Asn Pro Glu Asn Thr Val Phe Asp Ala Lys
                85                  90                  95

Arg Leu Ile Gly Arg Thr Trp Asn Asp Pro Ser Val Gln Gln Asp Ile
            100                 105                 110

Lys Phe Leu Pro Phe Lys Val Val Glu Lys Lys Thr Lys Pro Tyr Ile
        115                 120                 125

Gln Val Asp Ile Gly Gly Gly Gln Thr Lys Thr Phe Ala Pro Glu Glu
130                 135                 140

Ile Ser Ala Met Val Leu Thr Lys Met Lys Glu Thr Ala Glu Ala Tyr
145                 150                 155                 160

Leu Gly Lys Lys Val Thr His Ala Val Val Thr Val Pro Ala Tyr Phe
                165                 170                 175

Asn Asp Ala Gln Arg Gln Ala Thr Lys Asp Ala Gly Thr Ile Ala Gly
            180                 185                 190

Leu Asn Val Met Arg Ile Ile Asn Glu Pro Thr Ala Ala Ala Thr Ala
        195                 200                 205

Tyr Gly Leu Asp Lys Arg Glu Gly Glu Lys Asn Thr Leu Val Phe Asp
210                 215                 220

Leu Gly Gly Gly Thr Phe Asp Val Ser Leu Leu Thr Ile Asp Asn Gly
225                 230                 235                 240

Val Phe Glu Val Val Ala Thr Asn Gly Asp Thr His Leu Gly Gly Glu
                245                 250                 255

Asp Phe Asp Gln Arg Val Met Glu His Phe Ile Lys Leu Tyr Lys Lys
            260                 265                 270

Lys Thr Gly Lys Asp Val Arg Lys Asp Asn Arg Ala Val Gln Lys Leu
        275                 280                 285

Arg Arg Glu Val Glu Lys Ala Lys Arg Ala Leu Ser Ser Gln His Gln
290                 295                 300

Ala Arg Ile Glu Ile Glu Ser Phe Tyr Glu Gly Glu Asp Phe Ser Glu
305                 310                 315                 320

Thr Leu Thr Arg Ala Lys Phe Glu Glu Leu Asn Met Asp Leu Phe Arg
```

```
                     325                 330                 335
Ser Thr Met Lys Pro Val Gln Lys Val Leu Glu Asp Ser Asp Leu Lys
            340                 345                 350

Lys Ser Asp Ile Asp Glu Ile Val Leu Val Gly Gly Ser Thr Arg Ile
            355                 360                 365

Pro Lys Ile Gln Gln Leu Val Lys Glu Phe Phe Asn Gly Lys Glu Pro
            370                 375                 380

Ser Arg Gly Ile Asn Pro Asp Glu Ala Val Ala Tyr Gly Ala Ala Val
385                 390                 395                 400

Gln Ala Gly Val Leu Ser Gly Asp Gln Asp Thr Gly Asp Leu Val Leu
                405                 410                 415

Leu Asp Val Cys Pro Leu Thr Leu Gly Ile Glu Thr Val Gly Gly Val
                420                 425                 430

Met Thr Lys Leu Ile Pro Arg Asn Thr Val Val Pro Thr Lys Lys Ser
            435                 440                 445

Gln Ile Phe Ser Thr Ala Ser Asp Asn Gln Pro Thr Val Thr Ile Lys
            450                 455                 460

Val Tyr Glu Gly Glu Arg Pro Leu Thr Lys Asp Asn His Leu Leu Gly
465                 470                 475                 480

Thr Phe Asp Leu Thr Gly Ile Pro Pro Ala Pro Arg Gly Val Pro Gln
                485                 490                 495

Ile Glu Val Thr Phe Glu Ile Asp Val Asn Gly Ile Leu Arg Val Thr
                500                 505                 510

Ala Glu Asp Lys Gly Thr Gly Asn Lys Asn Lys Ile Thr Ile Thr Asn
            515                 520                 525

Asp Gln Asn Arg Leu Thr Pro Glu Glu Ile Glu Arg Met Val Asn Asp
            530                 535                 540

Ala Glu Lys Phe Ala Glu Asp Lys Lys Leu Lys Glu Arg Ile Asp
545                 550                 555                 560

Thr Arg Asn Glu Leu Glu Ser Tyr Ala Tyr Ser Leu Lys Asn Gln Ile
                565                 570                 575

Gly Asp Lys Glu Lys Leu Gly Gly Lys Leu Ser Ser Glu Asp Lys Glu
            580                 585                 590

Thr Met Glu Lys Ala Val Glu Glu Lys Ile Glu Trp Leu Glu Ser His
            595                 600                 605

Gln Asp Ala Asp Ile Glu Asp Phe Lys Ala Lys Lys Lys Glu Leu Glu
            610                 615                 620

Glu Ile Val Gln Pro Ile Ile Ser Lys Leu Tyr Gly Ser Ala Gly Pro
625                 630                 635                 640

Pro Pro Thr Gly Glu Glu Asp Thr Ala Glu Lys Asp Glu Ile
                645                 650
```

<210> SEQ ID NO 20
<211> LENGTH: 8
<212> TYPE: PRT
<213> ORGANISM: Artificial Sequence
<220> FEATURE:
<223> OTHER INFORMATION: GRP78 binding domain

<400> SEQUENCE: 20

```
Trp Ile Phe Pro Trp Ile Gln Leu
1               5
```